US008846057B2

(12) United States Patent
De Los Santos et al.

(10) Patent No.: US 8,846,057 B2
(45) Date of Patent: Sep. 30, 2014

(54) RECOMBINANT LIVE ATTENUATED FOOT-AND-MOUTH DISEASE (FMD) VACCINE CONTAINING MUTATIONS IN THE L PROTEIN CODING REGION

(75) Inventors: Teresa B. De Los Santos, Miller Place, NY (US); James J. Zhu, Niantic, CT (US); Fayna Diaz-San Segundo, Ronkonkoma, NY (US); Marvin J. Grubman, Southold, NY (US); Marla J. Koster, Cutchogue, NY (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 380 days.

(21) Appl. No.: 13/009,211

(22) Filed: Jan. 19, 2011

(65) Prior Publication Data

US 2011/0177123 A1    Jul. 21, 2011

Related U.S. Application Data

(60) Provisional application No. 61/296,273, filed on Jan. 19, 2010.

(51) Int. Cl.
*A61K 39/12* (2006.01)
*A61K 39/135* (2006.01)
*A61K 39/00* (2006.01)

(52) U.S. Cl.
CPC ....... *A61K 39/12* (2013.01); *C12N 2770/32134* (2013.01); *A61K 2039/522* (2013.01)
USPC .................................................... 424/216.1

(58) Field of Classification Search
None
See application file for complete search history.

(56) References Cited

FOREIGN PATENT DOCUMENTS

WO    WO 2009/150429    * 12/2009

OTHER PUBLICATIONS

Chinsangaram et al. (Vaccine; 1998;16 (16): 1516-1522).*
de los Santos et al. (Journal of Virology. Feb. 2009; 83 (4): 1800-1810).*

* cited by examiner

*Primary Examiner* — Shanon A Foley
(74) *Attorney, Agent, or Firm* — John D. Fado; Evelyn M. Rabin

(57) ABSTRACT

Previously we have identified a conserved domain (SAP, for SAF-A/B, Acinus, and PIAS) in the foot-and-mouth disease virus (FMDV) leader (L) protein coding region that is required for proper sub-cellular localization and function. Mutation of isoleucine 55 and leucine 58 to alanine (I55A, L58A) within the SAP domain resulted in a viable virus that displayed a mild attenuated phenotype in cell culture, along with altered sub-cellular distribution of L and failure to induce degradation of the transcription factor nuclear factor kappa-B. Here we report that inoculation of swine and cattle with this mutant virus results in the absence of clinical disease, the induction of a significant FMDV-specific neutralizing antibody response, and protection against subsequent homologous virus challenge. Remarkably, swine vaccinated with SAP mutant virus are protected against wild type virus challenge as early as two days post-vaccination suggesting that a strong innate as well as adaptive immunity is elicited. This variant could serve as the basis for construction of a live-attenuated FMD vaccine candidate.

7 Claims, 3 Drawing Sheets
(2 of 3 Drawing Sheet(s) Filed in Color)

RECOMBINANT LIVE ATTENUATED FOOT-AND-MOUTH DISEASE (FMD) VACCINE CONTAINING MUTATIONS IN THE L PROTEIN CODING REGION

This application claims the benefit of U.S. Provisional Application No. 61/296,273 filed Jan. 19, 2010, which is incorporated herein by reference in its entirety.

BACKGROUND OF THE INVENTION

1. Field of the Invention

This invention relates to a novel live attenuated FMD vaccine comprising mutated virulence determinants within the coding region of the SAP domain of the leader protein of FMDV wherein the mutated virulence determinants of the novel live FMD vaccine confer significant attenuation in swine and cattle as evidenced by absence of clinical disease, the induction of a significant FMDV-specific neutralizing antibody response, and protection against subsequent homologous virus challenge; and to the method of treating swine, cattle, goats, and sheep with the vaccine in order to protect swine, cattle, goats, and sheep against clinical FMD.

2. Description of the Relevant Art

Foot-and-mouth disease virus (FMDV) is the etiologic agent of FMD, a highly contagious disease that affects wild and domestic cloven-hoofed animals, including swine, cattle, sheep, goats, deer, and buffalo that quickly replicates in the host spreading to susceptible animals by contact and aerosol (Grubman and Baxt. 2004. *Clinical Micro. Rev.* 17: 465-493). FMD is considered one of the most contagious diseases of animal or man. The International Organization of Animal Health (OIE) includes FMD in the list A of diseases which requires the immediate official report of confirmed FMD cases and cessation of trading of susceptible animals including their products. FMD is enzootic in all world continents except for Australia and North America. Although the U.S. has been FMD-free since 1929 recent natural outbreaks in previously disease-free countries and the rapid advancement of world globalization, have significantly increased public awareness about this disease. Outbreaks in Taiwan (1997) and in the UK (2001, 2007) have resulted in losses to the agricultural industry surpassing $15 billion with more than 10 million animals slaughtered. A chemically inactivated vaccine is currently used in enzootic areas (Doel, T. R. 2003. *Virus Res.* 91:81-99) but FMD-free countries are reluctant to use this vaccine for several reasons: vaccine manufacturing requires a biosafety level 3 (BSL3) containment facility, the vaccine does not allow for differentiation between vaccinated and infected animals and there is a potential risk of deriving asymptomatic disease carriers upon exposure of vaccinated animals to infectious virus. As a result the OIE requires that countries that vaccinate to control FMD must wait 6 months after demonstrating, by serosurveillance, the absence of FMD before regaining FMD-free status, while countries that slaughter or vaccinate and then slaughter must only wait 3 months. Mayr et al. (2001. *Vaccine* 19:2152-2162) and Moraes et al. (2002. *Vaccine* 20:1631-1639) have constructed a recombinant vaccine delivered by a replication defective human adenovirus type 5 (Ad5) vector that can protect cattle and swine from clinical disease and viremia, allows unequivocal differentiation of vaccinated from infected animals, and does not require high containment facilities for vaccine production. However, similar to the inactivated vaccine, the Ad5 vaccine requires at least one week to induce a protective immune response and currently it is quite expensive to manufacture.

It has been reported that rapid and long lasting protection against viral infection is usually best achieved by vaccination with live-attenuated viral vaccines. Unfortunately, attempts to develop live-attenuated FMD vaccines have met with limited success. Instability of the mutant phenotype, excessive attenuation that results in failure to induce a protective immune response, differences in the degree of attenuation for individual species (e.g., swine vs. cattle) and the possibility of reversion to virulence, have stalled efforts in pursuing such an approach (Mowat et al. 1962. *Nature* 196:655-656; Mowat et al. 1969. *Arch. Virol.* 26:341-354; Martin and Edwards. 1965. *Res. Vet. Sci.* 36:196-201; Zhidkow and Sergeev. 1969. *Veterinariia* 10:29-31). With the advent of infectious FMDV cDNA it has been possible to introduce specific changes in the FMDV genome and evaluate the phenotypic changes after growth in cell culture and animals. As a result it is possible to test such virus variants as potential live-attenuated vaccine candidates (Rieder et al. 1993. *J. Virol.* 67:5139-5145; Rieder et al. 1994. *J. Virol.* 68:7092-7098; Piccone et al. 1995a. *J. Virol.* 69:5376-5382).

The virus is the prototype member of the Aphthovirus genus of the Picornaviridae family and consists of a positive strand RNA genome of about 8 kb surrounded by an icosahedral capsid containing 60 copies each of four structural proteins. Upon infection, the viral RNA is translated as a single polyprotein which is concurrently processed by three viral-encoded proteinases, leader ($L^{pro}$), 2A and $3C^{pro}$ into precursors and mature structural (VP1, VP2, VP3 and VP4) and non structural proteins ($L^{pro}$), 2A, 2B, 2C, 3A, 3B, $3C^{pro}$ and $3D^{pol}$) (Rueckert, R. R. 1996. In: *Field's Virology*, Fields et al. (eds), Lippincott-Raven, Philadelphia and New York, pages 609-654).

Studies in our laboratory have demonstrated that $L^{pro}$ plays a critical role in the pathogenesis of FMDV. In a hallmark discovery it was shown that deletion of the portion of the viral genome coding for the L protein region results in a viable attenuated, not transmissible (leaderless) virus that induced partial protection against challenge (Mason et al. 1997. *Virology* 227:96-102; Chinsangaram et al. 1998. *Vaccine* 16:1516-1522). Studies with this virus have significantly contributed to understanding some of the molecular mechanisms involved in FMDV virulence. The FMDV L protein is positioned at the N-terminus of the viral polyprotein. Translation of the polyprotein is initiated at two different AUGs which are separated by 84 nucleotides yielding two alternative forms of $L^{pro}$). Initiation at the first AUG results in Lab, an $L^{pro}$ form of 201 amino acids, and initiation at the second AUG results in Lb, an $L^{pro}$ form of 173 amino acids which is predominantly produced (Cao et al. 1995. *J. Virol.* 69:560-563; Piccone et al. 1995b. J. Virol. 69:4950-4956).

The FMDV L protein is a protease that in addition to cleaving itself from the nascent viral polyprotein, cleaves cellular proteins and modulates the host innate immune response (Strebel and Beck. 1986. *J. Virol.* 58:893-899; Devaney et al. 1988. *J. Virol.* 62: 4407-4409; Chinsangaram et al. 1999. *J. Virol.* 73: 9891-9898; Chinsangaram et al. 2001. *J. Virol.* 75: 5498-5503; de los Santos et al. 2006. *J. Virol.* 80:1906-1914; de los Santos et al. 2007. *J. Virol.* 81:12803-128151).

One of the reasons for the attenuation of the leaderless virus is the inability of this virus to block host cell translation, in particular, translation of type I interferon (IFNα/β) (Chinsangaram et al. 1999, supra). In most cell types, expression of IFN is induced in response to viral infection. Subsequently, IFN protein is secreted and binds to specific cell-surface receptors acting in an autocrine or paracrine manner. The interaction between IFN and its receptor induces a series of signal transduction events that lead to the expression of interferon stimulated genes (ISGs) which have antiviral and/or antiproliferative properties (Haller et al. 2006. *Virology* 344: 119-130; Honda et al. 2006. *Int. Immunol.* 17:1367-1378). Among the ISGs, the IFN induced dsRNA dependent protein kinase (PKR) and the IFN induced ribonuclease L (RNase L) have been shown to inhibit FMDV replication (Chinsangaram et al. 2001, supra; de los Santos et al. 2006, supra). Therefore, the L$^{pro}$ inhibition of host translation limits the synthesis of IFN protein and the IFN-triggered antiviral effects.

Recent data has demonstrated that L$^{pro}$, in addition to its effect on translation, also blocks the induction of IFNβ transcription, a very early response to viral infection (de los Santos et al. 2006, supra). In uninfected cells, transcription of IFNβ is not detectable, but upon viral infection latent transcription factors, including nuclear factor KB (NF-κB), interferon regulatory factors 3 and 7 (IRF3, IRF7) and the activating transcription factor 2/cellular Jun protein complex (ATF2/cJun, also named AP-1) are activated and translocated from the cytoplasm to the nucleus of the cell, where they bind to their respective IFNβ enhancer elements, thereby inducing gene expression (Honda et al., supra). Several studies have shown that one of the mechanisms employed by different viruses to antagonize the innate immune response is the inhibition of the induction of IFNβ transcription (Conzelmann, K.-K. 2005. *J. Virol.* 79: 5241-5248; Haller et al., supra). Among picornaviruses, it has been reported that poliovirus causes the degradation of several proteins, including the p65/RelA subunit of NF-κB and the RNA helicase MDA-5, resulting in reduced IFNβ transcription (Barral et al. 2007. *J. Virol.* 81:3677-3684; Neznanov et al. 2005. *J. Biol. Chem.* 280: 24153-24158).

Our group has shown that during FMDV infection down-regulation of IFNβ transcription is associated with L$^{pro}$ dependent degradation of the p65/RelA subunit of NF-κB (de los Santos et al. 2006, supra; de los Santos et al. 2007, supra). Interestingly, our studies showed that L$^{pro}$ translocates to the nucleus of infected cells and there is a correlation between the translocation of L$^{pro}$ and the decrease in the amount of nuclear p65/RelA. However, it still remains unclear how FMDV L$^{pro}$ induces p65/RelA degradation since highly conserved L$^{pro}$ cleavage sites have not been found in the p65/RelA protein primary sequence nor have defined p65/RelA degradation products been detected during FMDV infection (de los Santos et al. 2007, supra).

Recently, the availability of bioinformatic tools has resulted in the prediction of multiple domains within the L protein, one of which is a putative SAF-A/B, Acinus and PIAS (SAP) domain, between amino acids 47 and 83, (following the numbering from the Lb form of L$^{pro}$). This domain, SAP, has been described in other proteins which are involved in transcriptional control (Aravind and Koonin. 2000. *TIBS* 25:112-114).

Here we report the effects of a double point mutation in the coding region of the functional SAP domain of FMDV L$^{pro}$ and complete attenuation in vivo. Animals infected with the doubly mutated virus were protected when challenged with virulent FMDV. Such attenuated viruses permit the rational design of live attenuated FMD vaccines. Live-attenuated FMD vaccines can potentially induce longer protection than current vaccines thereby reducing the need for bi- or tri-annual vaccination to ensure protection. Thus, there is a need for new FMD vaccines that display a stable and a significant attenuated phenotype which can be used to protect domestic cloven-hoofed animals (e.g., swine, cattle, goats, and sheep) from FMD.

SUMMARY OF THE INVENTION

We have discovered that a double mutation (two single point mutations) in the coding region of a functional SAP domain of FMDV L$^{pro}$ which in vitro displayed moderate attenuation of FMDV as evidenced by inadequate sub-cellular distribution of the Lb protein and an inability to induce degradation of the transcription factor nuclear factor kappa-B, surprisingly conferred significant attenuation in vivo, i.e., there was an absence of clinical disease in both swine and cattle inoculated with this mutated virus, there was a significant FMDV-specific neutralizing antibody response induced, and the swine were protected against subsequent homologous virus challenge as early as two days post vaccination.

In accordance with this discovery, it is an object of the invention to provide a FMD vaccine comprising a FMDV having a double mutation in the coding region of the SAP domain of FMDV L$^{pro}$.

It is also an object of the invention to provide a mutated FMDV comprising a mutation in the coding region of the SAP domain of FMDV L$^{pro}$, a modification resulting in attenuation of FMDV.

It is a further object of the invention to provide a mutated FMDV comprising a double mutation in the coding region of the SAP domain of FMDV L$^{pro}$, a modification resulting in attenuation of FMDV.

An added object of the invention is to provide immunogenic compositions comprising a viable modified FMDV comprising a mutation in the coding region of the SAP domain of FMDV L$^{pro}$.

An additional object of the invention is to provide immunogenic compositions comprising a viable modified FMDV comprising a double mutation in the coding region of the SAP domain of FMDV L$^{pro}$.

An additional object of the invention is to provide a rationally designed live attenuated FMD vaccine which lessens severity of FMD.

Another object of the invention is to provide a rationally designed live attenuated FMD vaccine effective to protect an animal from clinical FMD when challenged with virulent FMDV.

Another object of the invention is to provide a FMD vaccine comprising a FMDV having a double mutation in the coding region of the SAP domain of FMDV L$^{pro}$ and additional mutation/s resulting in more attenuation and a decreased probability of reversion.

A further object of the invention is to provide a FMD vaccine comprising a FMDV having a double mutation in the coding region of the SAP domain of FMDV L$^{pro}$ and additional mutation/s that allow a serological distinction between vaccinated animals and animals infected with FMDV.

A further object of the invention is to provide a FMD vaccine comprising a FMDV having a double mutation in the coding region of the SAP domain of FMDV L$^{pro}$ and additional mutations that result in more attenuation and a decreased probability of reversion and further allow a serological distinction between vaccinated animals and animals infected with FMDV.

A still further object of the invention is to provide a method for protecting an animal against FMD by administering an effective amount of rationally designed live attenuated FMD vaccine.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIG. 2A depicts the growth curves. BHK-21 or EBK cells were infected with the indicated viruses and after 1 h, unabsorbed virus was removed by washing with 150 mM NaCl, 20 mM MES (pH=6.0) followed by addition of complete media. Samples were taken at 1, 3, 6 and 24 hours post infection (hpi) and virus titers were determined by plaque assay on BHK-21 cells. (Reported values display one out of three representative experiments with similar results). FIG. 2B shows BHK-21 cells were infected with similar amounts of viruses and treated as described in panel A, but media with gum tragacant overlay was added and plaques were stained at 40 hpi.

DETAILED DESCRIPTION OF THE INVENTION

Figure 1:
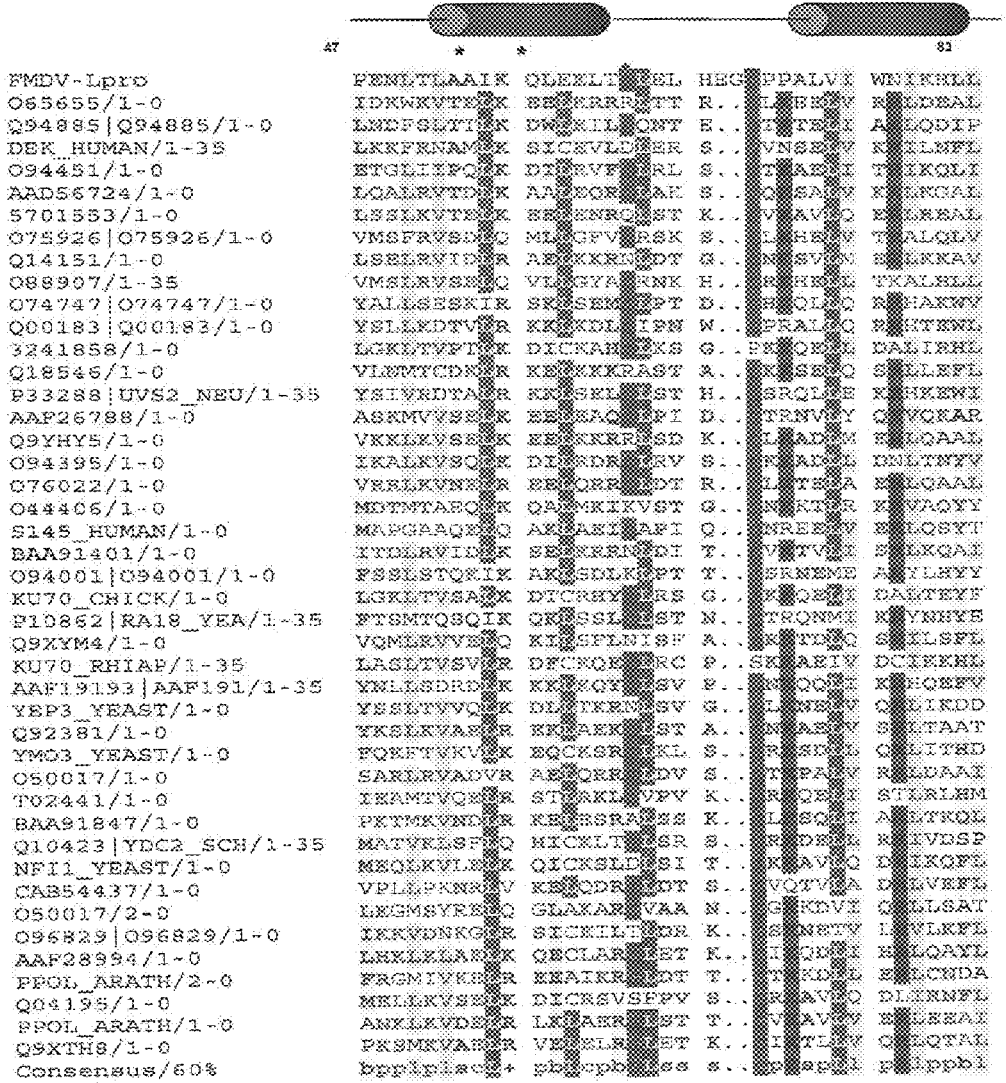
FIG. 1 depicts the alignment of FMDV $L^{pro}$ partial amino acid sequence. $L^{pro}$ protein sequence (SEQ ID NO:1) was aligned to all available sequences (SEQ ID NOs: 2-45) utilizing SMART software. Depicted are sequences in single letters between amino acids 47-88 and a schematic cartoon displaying approximate location of predicted α-helices (green ovals). Asterisks (*) mark location of amino acids targeted by mutagenesis. α: positive charged amino acids (H,K,R); b: amino acids with a large or bulky side chain (E,F,H,I,K,L,M,Q,R,W,Y); c: charged amino acids (D,E,H,K,R); I: aliphatic amino acids (I,L,V); p: polar amino acids (C,D,E,H,K,N,Q,R,S,T); s: amino acids with a small side chain (A,C,D,G,N,P,S,T,V); and gray highlighted: amino acids with equal to or greater than 60% of homology in the alignment.

We have introduced single or double point mutations in conserved amino acid residues (I55 and L58) contained within the L protein SAP domain. Characterization of the mutant virus in cell culture (in vitro) showed that the double mutant I55A, L58A, maintained some of its functional properties but displayed a mildly attenuated phenotype in that cells infected in vitro with the I55A, L58A doubly mutated FMDV appeared to prevent cleavage of transcription factor nuclear factor kappa-B (NF-κB). In this study, we have utilized this mutant virus to inoculate swine/cattle and compared responses with WT FMDV inoculated animals. No signs of disease were observed in the animals inoculated with the SAP mutant virus even when the dose was 100 times higher than for the WT. In contrast, animals inoculated with WT FMDV developed disease at 2 dpi. Interestingly, a strong neutralizing antibody response was observed in both species inoculated with the mutant virus and challenged of swine with homologous WT virus resulted in complete protection. Further, the double point mutation was stable; no reversion to WT sequence was observed in any of the inoculated animals. Remarkably, animals vaccinated with the SAP mutant virus are protected against WT virus challenge as early as 2 days post vaccination, suggesting that the mutant strain is able to mount a strong innate immune response in addition to induce protective adaptive immunity. These results indicate that the double SAP mutant virus could be used as the basis for construction of a new live-attenuated vaccine candidate against FMD and further as a platform to incorporate mutations, for example, to ensure serological distinction between vaccinated animals and animals infected with FMDV or to decrease the probability of reversion to virulence.

We have earlier reported that $L^{pro}$ antagonizes the innate immune response by blocking the expression of IFN. At least two mechanisms are involved in this function: the shut off of host cell translation resulting in lower levels of IFN protein expression, and the interference in the induction of IFNβ transcription. $L^{pro}$ cleaves the eukaryotic translation initiation factor eIF-4G, which is required for cap-dependent mRNA translation without affecting the IRES-dependent translation of viral RNA and thus, the virus takes advantage of decreased levels of IFN protein to establish a productive infection (Chinsangaram et al. 1999, supra; Grubman et al. 2008. FEMS Immunol. Med. Microbiol. 53:8-17; Kirchweger et al. 1994. J. Virol. 68:5677-5684). In addition, $L^{pro}$ induces the degradation of the p65/RelA subunit of the transcription factor NF-κB and this degradation is associated with $L^{pro}$ nuclear localization (de los Santos et al. 2007, supra). A block in the up-regulation of IFNβ transcription also results in lower levels of IFN protein (de los Santos et al. 2006, supra).

The availability of multiple FMDV protein sequences (Carrillo et al. 2005. J. Virol. 79:6487-6504), the high-resolution crystal structure of $L^{pro}$ (Guarné et al. 1998. EMBO J. 17:7469-7479) and powerful software tools (Letunic et al. 2006. Nucleic Acids Res. 34:257-260), have allowed us to predict that a conserved SAP domain is situated between amino acids 47 and 83 of Lb. We demonstrate that this domain is important for $L^{pro}$ function. A double point mutation in the SAP domain resulted in a moderately attenuated virus phenotype in vitro yielding lower titers and a smaller plaque size. Although the phenotype was not as clear-cut as in the case of the $L^{pro}$ deletion in leaderless virus, it was indicative of a role of this domain in FMDV virulence. Early translocation of mutant $L^{pro}$ from the cytoplasm to the nucleus of infected cells was slightly delayed. However, by 6 hpi, mutant $L^{pro}$ in contrast to WT $L^{pro}$, was absent from the nuclei of infected cells. Failure in nuclear retention has been reported for another SAP containing protein, PIAS3L, when this domain was mutated (Duval et al. 2003. FEBS Lett. 554:111-118). PIAS3L requires an intact SAP box, in conjunction with a RING and a PINIT domain for proper nuclear localization and retention (Duval et al., supra). Perhaps FMDV $L^{pro}$ depends on an intact SAP domain for docking in the nucleus of infected cells, allowing for interactions with host proteins that might be involved in regulating an antiviral response.

A further observation in this study was the absence of NF-κB degradation upon infection with FMDV double SAP mutant even though these mutations did not affect the catalytic activity of $L^{pro}$. With the exception of leaderless virus, no other viable FMDV $L^{pro}$ mutant has been previously reported. In vitro studies using mutant recombinant protein or plasmid transient transfection have been very informative, demonstrating that residue C23 is required for the protease enzymatic activity and is utilized by $L^{pro}$ for self-cleavage from the viral polyprotein and cleavage of the translation initiation factor eIF-4G (Devaney et al. 1988. J. Virol. 62:4407-4409; Mayer et al. 2008. J. Virol. 82:4656-4659; Piccone et al. 1995b, supra; Roberts and Belsham. 1995. Virology 213:140-146). Recently, Mayer et al., (supra) using rabbit reticulocyte lysates have shown that $L^{pro}$ residue L115 is also a determinant of self and eIF-4G cleavage specificity. Utilizing a recombinant cardiovirus expressing $L^{pro}$ in the absence of any other FMDV protein, we also demonstrated that the catalytic activity of $L^{pro}$ is required for NF-κB degradation; mutation of the catalytic residue C23 prevented degradation. Unfortunately, the mechanism employed by $L^{pro}$ to cause NF-κB degradation is still unclear.

As mentioned above, $L^{pro}$ SAP mutations did not affect $L^{pro}$ enzymatic activity; self and eIF-4G processing proceeded almost normally. We did observe that degradation of the eIF-4G cleavage products was delayed in cells infected with the double mutant. Mutation of the SAP domain partially affects the interaction between $L^{pro}$ and eIF-4G; quantitative kinetics studies need to be performed. It has been reported that FMDV 3C can also cleave eIF-4G at later times post FMDV infection (Strong and Belsham. 2004. *J. Gen. Virol.* 85:2953-2962), thus it is possible that the $L^{pro}$ SAP mutant interferes with the 3C/eIF-4G interaction. Our results however, suggest that 3C from double mutant SAP virus behaves normally since processing of the viral polyprotein proceeded similarly for the mutant and WT viruses.

The levels of several transcripts including cytokines, chemokines and ISGs were significantly higher after infection with FMDV $L^{pro}$ SAP mutant #49 as compared to WT infection, indicating that disruption of the SAP domain prevented $L^{pro}$ inhibition of NF-κB dependent transcription. SAP domains are involved in protein-protein interactions. This motif is required for the repressive activity of PIASy on STAT1 mediated gene activation (Liu et al. 2001. *Proc. Natl. Acad. Sci. USA* 98:3203-3207) and it has been proposed that several members of the PIAS protein family negatively regulate NF-κB and STAT signaling affecting the expression of more than 60 genes (Shuai, K. 2006. *Nat. Rev. Immunol.* 5:593-605). Furthermore, the specific role of PIAS proteins in the regulation of NF-κB activity has been examined in vivo utilizing PIAS1 null mice (Liu et al. 2005. *Mol. Cell. Biol.* 25:1113-1123). These studies demonstrated that in the absence of PIAS only a subset of NF-κB regulated genes is affected (about 48%) suggesting that there might be alternative mechanisms, independent of PIAS1, for NF-κB regulation.

More interestingly, Jang et al. (2004. *J. Biol. Chem.* 279: 24873-24880) have provided evidence that the N-terminal region of PIAS3, which contains a SAP domain, is necessary for binding to the p65/RelA subunit of NF-κB thereby blocking the transcriptional activation. Furthermore, an LXXLL signature motif of PIAS3 is involved in this physical interaction. Although not identical, this motif resembles the IQKL sequence present in FMDV $L^{pro}$. Our results suggest that this putative interaction may be involved in docking $L^{pro}$ in the nucleus of infected cells where $L^{pro}$ dependent p65/RelA degradation takes place during FMDV infection.

SAP domains are also found in several proteins displaying DNA binding activity and the contact with defined A/T rich sequences found in matrix attachment regions (MARs) of chromatin is mediated by the predicted alpha helices delimited by the SAP box (Kipp et al. 2000. *Mol. Cell. Biol.* 20:7480-7489). Protein interactions with MARs regions determine the chromatin architecture in zones of interactions with the nuclear matrix. Interestingly, several viral proteins have been shown to localize to these regions, leading to the proposal that viral protein interaction with MARs regions may have a role in blocking host antiviral activities (Everett and Chelbi-Alix. 2007. *Biochimie* 89:819-830). The presence of a SAP domain may allow FMDV $L^{pro}$ to localize to similar nuclear regions globally affecting the function of transcription factors situated in close proximity during viral infection.

Our results provide new insights into the mechanism used by FMDV to escape the immune response. Structure function analysis of $L^{pro}$ has demonstrated that in addition to the proteinase activity, an intact protein motif, SAP, is required for FMDV virulence. A more detailed understanding of the interactions between FMDV $L^{pro}$ and/or other viral proteins and the host at the molecular level, will help in the development of specific antiviral strategies that could limit virus spread.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions at those sequences as defined above.

By "variants" substantially similar sequences are intended. For nucleotide sequences, conservative variants include those sequences that, because of the degeneracy of the genetic code, encode the amino acid sequence of the SAP and $L^{pro}$ of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, activity of the doubly mutated $L^{pro}$ as described herein. Such variants may result from, for example, genetic polymorphism or from human manipulation. Biologically active variants of the doubly mutated $L^{pro}$ of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired doubly mutated $L^{pro}$ activity. Obviously, the mutations that will be made in the DNA encoding the variant must not place the sequence out of reading frame and preferably will not create complementary regions that could produce secondary mRNA structure.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

It is furthermore to be understood that the isolated polynucleotide molecules and the isolated RNA molecules of the present invention include both synthetic molecules and molecules obtained through recombinant techniques, such as by in vitro cloning and transcription.

As used herein, the term "FMD" encompasses disease signs in swine, cows, sheep, and goats caused by a FMDV infection. Examples of such signs include, but are not limited to: fever, lameness and vesicular lesions on the feet, tongue, snout and teats.

The terms "foot and mouth disease virus" and "FMDV", as used herein, unless otherwise indicated, mean any strain of FMD viruses.

The term "open reading frame", or "ORF", as used herein, means the minimal nucleotide sequence required to encode a particular FMDV protein without an intervening stop codon.

Terms such as "suitable host cell" and "appropriate host cell", unless otherwise indicated, refer to cells into which RNA molecules (or isolated polynucleotide molecules or viral vectors comprising DNA sequences encoding such RNA molecules) of the present invention can be transformed or transfected. "Suitable host cells" for transfection with such RNA molecules, isolated polynucleotide molecules, or viral vectors, include mammalian, particularly porcine, bovine, caprine, and ovine cells.

A "functional virion" is a virus particle that is able to enter a cell capable of hosting a FMDV, and express genes of its particular RNA genome (either an unmodified genome or a genetically modified genome as described herein) within the cell. Cells capable of hosting a FMDV include, for example, baby hamster kidney cells (e.g., BHK-21 cells) and swine kidney cells (e.g., IBRS-2 cells). Other cells may also serve as suitable host cells for FMD virions, e.g., bovine kidney cells (LF-BK cells) and primary embryonic bovine kidney (EBK) cells.

The term "immune response" for purposes of this invention means the production of antibodies and/or cells (such as T lymphocytes) that are directed against, or assist in the decomposition or inhibition of, a particular antigenic epitope or particular antigenic epitopes. The phrases "an effective immunoprotective response", "immunoprotection", and like terms, for purposes of the present invention, mean an immune response that is directed against one or more antigenic epitopes of a pathogen so as to protect against infection by the pathogen in a vaccinated animal. For purposes of the present invention, protection against infection by a pathogen includes not only the absolute prevention of infection, but also any detectable reduction in the degree or rate of infection by a pathogen, or any detectable reduction in the severity of the disease or any sign or condition resulting from infection by the pathogen in the vaccinated animal as compared to an unvaccinated infected animal. An effective immunoprotective response can be induced in animals that have not previously been infected with the pathogen and/or are not infected with the pathogen at the time of vaccination. An effective immunoprotective response can also be induced in an animal already infected with the pathogen at the time of vaccination.

An "antigenic epitope" is, unless otherwise indicated, a molecule that is able to elicit an immune response in a particular animal or species. Antigenic epitopes are proteinaceous molecules, i.e. polypeptide sequences, optionally comprising non-protein groups such as carbohydrate moieties and/or lipid moieties.

In a further preferred embodiment, an antigenic epitope of the genetically modified FMDV of the present invention is a detectable antigenic epitope. Such isolated polynucleotide molecules and the FMD viruses they encode are useful, inter alia, for studying FMDV infections in cows, swine, goats, and sheep, determining successfully vaccinated cows, swine, goats, and sheep, and/or for distinguishing said vaccinated animals from cows, swine, goats, and sheep infected by a WT FMDV. Preferably, such isolated polynucleotide molecules further contain one or more mutations that genetically disable the encoded FMDV in its ability to produce FMD, and more preferably are able to elicit an effective immunoprotective response in a porcine animal against infection by a FMDV.

Antigenic epitopes that are detectable, and the sequences that encode them, are known in the art. Techniques for detecting such antigenic epitopes are also known in the art and include serological detection of antibody specific to the heterologous antigenic epitope by means of, for example, Western blot, ELISA, or fluorescently labeled antibodies capable of binding to the antibodies specific to the heterologous antigenic epitope. Techniques for serological detection useful in practicing the present invention can be found in texts recognized in the art, such as Coligan, J. E., et al. (eds), 1998, *Current Protocols in Immunology*, John Willey & Sons, Inc., which is hereby incorporated by reference in its entirety. Alternatively, the antigenic epitope itself can be detected by, for example, contacting samples that potentially comprise the antigenic epitope with fluorescently-labeled antibodies or radioactively-labeled antibodies that specifically bind to the antigenic epitopes.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., *Remington's Pharmaceutical Science*, 18th ed., 1990, Mack Publishing, which is incorporated herein by reference.

Adjuvants can be used in the vaccine of the present invention and can include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 µg/ml Quil A, 100 µg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 µg/ml Quil A, and 50 µg/ml cholesterol. Other immunomodulatory agents that can be included in the vaccine include, e.g., one or more interleukins, interferons, or other known cytokines.

An effective amount of any of the above-described vaccines can be determined by conventional means, starting with a low dose of virus, plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies.

The effective dose amount of virus, infectious RNA molecule, plasmid, or viral vector, of the present invention can be determined using known techniques, taking into account factors that can be determined by one of ordinary skill in the art such as the weight of the animal to be vaccinated.

EXAMPLES

Having now generally described this invention, the same will be better understood by reference to certain specific examples, which are included herein only to further illustrate the invention and are not intended to limit the scope of the invention as defined by the claims.

Example 1

Discovery of a Putative SAP Domain in FMDV $L^{pro}$

A consensus sequence of $L^{pro}$ was obtained from the alignment of all available FMDV amino acid sequences in GenBank. The consensus sequence was used in the annotation of protein domains with the Simple Modular Architecture Research Tool (SMART) (Letunic et al., supra).

Utilizing the SMART software we have found that between amino acids 47 to 83 of the FMDV $L^{pro}$ coding sequence (following the numbering of Lb) there is a conserved sequence motif that resembles a previously defined SAP domain in cellular proteins (Aravind and Koonin, supra) (FIG. 1). Comparison of the $L^{pro}$ sequence to the sequence profile of known SAP domains revealed that greater than 80% of the $L^{pro}$ amino acids within this region are present in the profile. Additionally, the three-dimensional structure of the $L^{pro}$ sequence (Guarné et al., supra) shared the same α-helix-turn-α helix structure found in SAP domains (Aravind and Koonin, supra). Despite the presence of a two amino acid insertion between the two α-helices in $L^{pro}$, the data support the presence of a SAP domain within $L^{pro}$.

Example 2

Cell Cultures and Viruses

BHK-21 cells (baby hamster kidney cells strain 21, clone 13, ATCC CL10), obtained from the American Type Culture Collection (ATCC, Manassas Va.) were used to propagate virus stocks and to measure virus titers. BHK-21 cells were maintained in minimal essential medium (MEM, GIBCO BRL, Invitrogen, Carlsbad, Calif.) containing 10% calf serum and 10% tryptose phosphate broth supplemented with 1% antibiotics and non-essential amino acids. Primary bovine embryonic kidney cells (EBK) were provided by the Animal, Plant, and Health Inspection Service, National Veterinary Service Laboratory, Ames, Iowa. These cells were maintained in MEM containing 10% fetal bovine serum (FBS) and supplemented with 1% antibiotics and non-essential amino acids. Cell cultures were incubated at 37° C. in 5% $CO_2$.

FMDV A12-WT was generated from the full-length serotype A12 infectious clone, pRMC35 (Rieder et al. 1993, supra) and A12-LLV2 (leaderless virus) was derived from the infectious clone lacking the Lb coding region, pRM-LLV2 (Piccone et al. 1995a, supra). A12#47, A12#48 and A12#49 mutant viruses were derivatives of A12-WT constructed by site directed mutagenesis as described below. Viruses were propagated in BHK-21 cells and were concentrated by polyethylene glycol precipitation, titrated on BHK-21 cells, and stored at −70° C.

Example 3

Construction of Mutant Viruses

Mutant FMDV viruses were constructed by introducing specific nucleotide changes in the cDNA of the respective infectious clones utilizing a QuickChange® mutagenesis kit (Stratagene, La Jolla, Calif.) following the manufacturer's directions. In order to determine if the putative SAP domain is important for $L^{pro}$ function, we mutated two residues at positions 55 or 58, individually (A12#47 and A12#48) or in combination (A12#49). We selected these amino acids based on previous studies with PIAS3, a SAP containing protein, where it was reported that mutation of a similar region altered PIAS3 nuclear localization and retention (Duval et al., supra).

For FMDV mutants, plasmid pRMC35 and oligonucleotide pairs that annealed to nucleotide (nt) positions 147-188 considering the AUG start codon of Lb as nt 1, were used as follows: I55A_FW: 5' CTCACACTAGCAGCCGCCAAA-CAGCTGGAGGAACTCACAGGG (SEQ ID NO:46) and I55A_RW: 5'CCCTGTGAGTTCCTCCAGCTGTTTG-GCGGCTGCTAGTGTGAG (SEQ ID NO:47) for A12#47, L58A_FW: 5'CTCACACTAGCAGCCATCAAACAGGCG-GAGGAACTCACAGGG (SEQ ID NO:48) and L58A_RW: 5'CCCTGTGAGTTCCTCCGCCTGTTTGATG-GCTGCTAGTGTGAG (SEQ ID NO:49) for A12#48 and I55A, L58A_FW: 5'CTCACACTAGCAGCCGCCAAA-CAGGCGGAGGAACTCACAGGG (SEQ ID NO:50) and I55A, L58A_RW: 5'CCCTGTGAGTTCCTCCGCCT-
GTTTGGCGGCTGCTAGTGTGAG (SEQ ID NO: 51) for
A12#49.

Example 4

FMDV Cell Infections

Cultured cell monolayers were infected with FMDV at the indicated multiplicity of infection (MOI's) for 1 h at 37° C. After adsorption, cells were rinsed and incubated with MEM at 37° C. For kinetics of growth or indirect immunofluorescence analyses (IFA) of FMDV infected cells, unabsorbed virus was removed by washing the cells with a solution containing 150 mM NaCl in 20 mM morpholineethanesulfonic acid (MES) pH=6.0, before adding MEM and proceeding with the incubation.

Example 5

Figure 2:
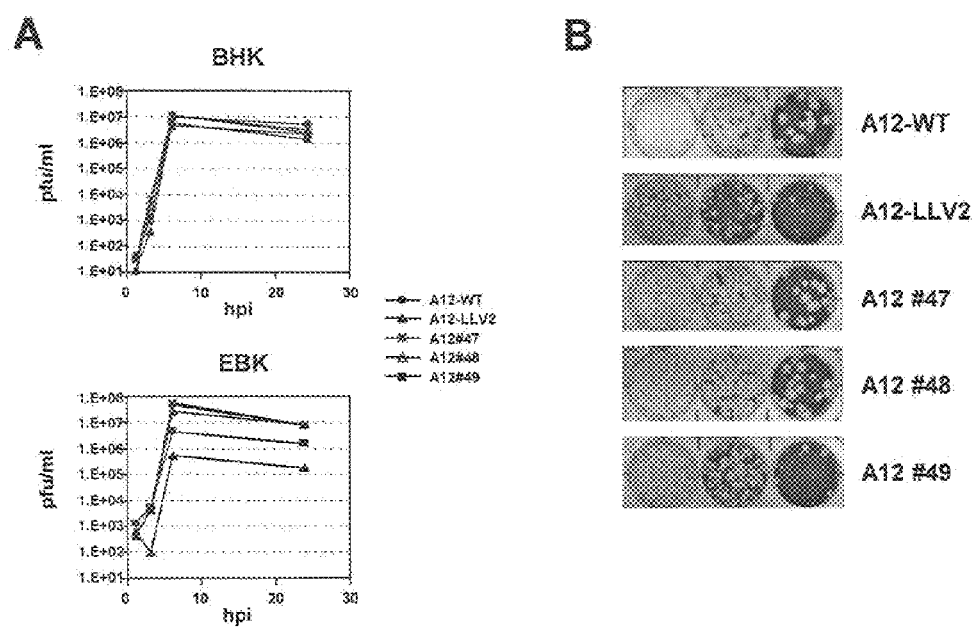
FIGS. 2A-B depict the kinetics of growth and plaque morphology.

In Vitro Characterization of FMDV Containing Mutations in the $L^{pro}$ SAP Domain; Viral Growth Viruses derived from transfected cells were passaged 4 times in BHK-21 cells and the $L^{pro}$ coding region of the resulting viruses was sequenced to confirm that the only changes were at the mutated sites. FIG. 2 shows the kinetics of growth of the mutant viruses in two different cell types. In BHK-21 cells all viruses grew with similar kinetics reaching final titers with differences of less than half log with respect to WT virus. In EBK cells the growth differences between WT and some of the mutant viruses were more pronounced. Leaderless virus, A12-LLV2, (Piccone et al., 1995) was included for reference and grew to a final titer ~50-fold lower than that of the WT virus (Chinsangaram et al. 1999, supra). Interestingly, A12#49 (double SAP mutant) grew to a final titer of about 5-fold lower than WT virus, whereas A12#47 and A12#48 (single SAP mutants) grew to similar titers as WT virus. Regarding plaque size, A12#47 and A12#48, resembled A12-WT virus and A12#49 was more related to the small plaque phenotype of A12-LLV2. These results indicated that disruption of the predicted signature motif of the SAP domain requires at least mutations at two sites and affects the growth characteristics of FMDV, but that the double mutant is only partially attenuated.

Example 6

Figure 3:
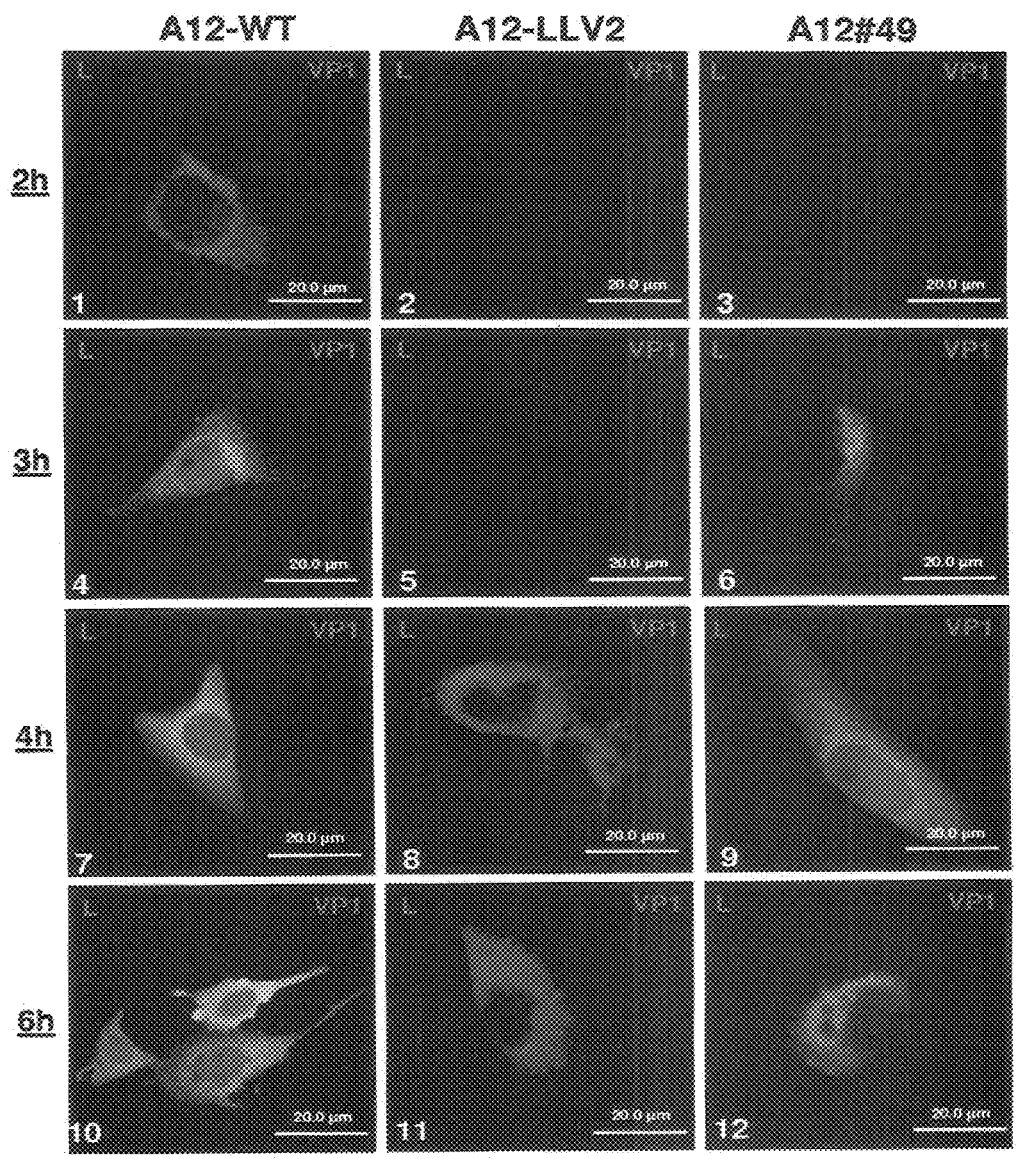
FIG. 3 depicts the IFA of $L^{pro}$ during FMDV infection. LF-BK cells were infected at MOI=10 with wild type FMDV (A12-WT) (panels 1, 4, 7 and 10), Leaderless FMDV (A12-LLV2) (panels 2, 5, 8 and 11) or double FMDV SAP mutant (A12#49) (panels 3, 6, 9 and 12) and were fixed at different times post-infection. Viral protein $L^{pro}$ was detected using a rabbit polyclonal Ab and an Alexa Fluor 488 conjugated secondary Ab. Viral protein VP1 was detected using mouse mAb 6HC4 and an Alexa Fluor 594 conjugated secondary Ab.

In vitro Characterization of FMDV Containing Mutations in the $L^{pro}$ SAP Domain; Nuclear Retention We have previously reported that during FMDV infection $L^{pro}$ progressively translocated to the nucleus of infected cells (de los Santos et al. 2007, supra). We looked at the subcellular localization of the various $L^{pro}$ mutants by immunefluorescence analysis (IFA) (FIG. 3). We analyzed the subcellular localization of $L^{pro}$ in the SAP mutants. In LF-BK cells infected with the single mutant viruses (A12#47 and A12#48) the translocation of $L^{pro}$ into the nucleus was indistinguishable from A12-WT. In contrast, the double SAP mutant (A12#49) displayed a distinct phenotype. At the beginning of the infection and up to 4 hpi, $L^{pro}$ of A12#49 was observed in the cytoplasm and then progressively appeared in the nucleus of the infected cells (FIG. 3 panels 3, 6 and 9) similar to A12-WT (FIG. 3 panels 1, 4 and 7). We observed that nuclear translocation of $L^{pro}$ was slightly delayed for A12#49. However, by 6 hpi almost no $L^{pro}$ nuclear staining was detected in cells infected with A12#49 in contrast to cells infected with A12-WT (FIG. 3 panels 12 and 10 respectively). Most of $L^{pro}$ was distributed throughout the cytoplasm concentrated in granules, as eventually observed for several other FMDV viral proteins when infection is well established. As a control, infection with A12-LLV2 did not display any $L^{pro}$ staining (FIG. 3 panels 2, 5, 8 and 11). These observations led us to conclude that mutation of the predicted SAP domain prevented $L^{pro}$ nuclear accumulation during the course of infection.

Example 7

In Vivo Swine Experiments

Fifteen 20-30 kg Yorkshire cross or Yorkshire/bluepoint gilts were divided into five groups of three animals each, housed in separate rooms, double fenced to avoid contact among the animals after inoculation. Each group of animals was inoculated intradermally (ID) in the rear left heel bulb with A12-IC (WT FMDV), $10^5$ or $10^6$ plaque forming units (pfu), or A12#49 (FMDV double SAP mutant) at a dose of $10^5$, $10^6$ or $10^7$ pfu/animal. Twenty one days after inoculation, the three groups inoculated with A12#49 were challenged ID in the right heel bulb pad with $1\times10^5$ pfu of A12-IC. Rectal temperature data and clinical signs, including lameness and vesicular lesions were recorded daily for 28 days. Temperature of over 40° C. for two or more consecutive days was considered to constitute a fever. Plasma, and nasal samples were collected daily for the first week and weekly thereafter. Serum samples were collected at 4 dpi and every week for 28 days.

As summarized in Table 1, none of the swine inoculated with A12#49 (SAP mutant) developed clinical signs of disease or shed virus in nasal secretions. Virus, at levels lower than 5 pfu/ml was detected in the nasal swabs of one animal inoculated with $10^7$ pfu of A12#49. All animals inoculated with WT virus developed disease and viremia that lasted for at least 3 days after the onset. In addition these animals shed virus in nasal secretions. The levels of neutralizing antibodies were determined at 4 and 7 dpi. Although no viremia was detected in the A#49 inoculated swine the levels of FMDV-specific neutralizing antibodies was between 1000 and 2000 $PRN_{70}$ as compared to 8000 and 16000 $PRN_{70}$ for the WT virus inoculated animals.

Example 8

In Vivo Cattle Experiments

Two Holstein cows (about 300-400 lbs each) housed in two separate rooms, were inoculated intradermally in the tongue with $10^4$ pfu of A12-IC FMDV (WT) or $10^6$ of A12#49 (double SAP mutant). Rectal temperature data and clinical signs, including lameness and vesicular lesions were recorded daily for 28 days. Plasma, nasal and oral samples were collected daily for the first week and weekly thereafter. Serum samples were collected at 4 and 7 dpi.

In cattle, viremia was detected in both, WT and A12#49 inoculated animals, however only virus was shed in the nasal secretion of the animal inoculated with WT virus even when the inoculation dose was 100 times lower than for the mutant. Although the levels of neutralizing antibodies were lower at 4 dpi for the mutant inoculated animal (16 vs. 128 $PRN_{70}$) by 7 dpi they reached levels comparable to WT (8000 vs. 4000 $PRN_{70}$).

TABLE 1

Clinical outcome and presence of neutralizing antibodies in animals inoculated with FMDV wild type (A12-IC WT) and FMDV SAP mutant (A12#49 SAP mutant) viruses.

| Inoculum | Dose[a] | Species | Viremia (dpc, day of onset, duration)[b] | No. of lesions (day of onset)[c] | PFU in nasal swabs (dpc, day of onset, duration)[d] | Neutralizing antibodies $PRN_{70}$[e] 4 dpc | 7 dpc |
|---|---|---|---|---|---|---|---|
| A12-IC WT | $1 \times 10^5$ | Porcine | $4.53 \times 10^2$ pfu/ml (3, 2, 3) | 10 (2) | $1.54 \times 10^2$ pfu/ml (4, 3, 3) | 32 | 8000 |
| A12-IC WT | $1 \times 10^6$ | Porcine | $8.84 \times 10^2$ pfu/ml (2, 1, 3) | 12 (2) | $7.30 \times 10^1$ pfu/ml (1, 1, 5) | 32 | 16000 |
| A12#49 SAP mutant | $1 \times 10^5$ | Porcine | Neg.[f] | 0 | Neg. | 32 | 1000 |
| A12#49 SAP mutant | $1 \times 10^6$ | Porcine | Neg. | 0 | Neg. | 32 | 2000 |
| A12#49 SAP mutant | $1 \times 10^7$ | Porcine | Neg. | 0 | Neg. | 32 | 2000 |
| A12-IC WT | $1 \times 10^4$ | Bovine | $1.20 \times 10^4$ pfu/ml (4, 3, 3) | 2 (5) | $1.00 \times 10^5$ pfu/ml (5, 3, 3) | 128 | 4000 |
| A12#49 SAP mutant | $1 \times 10^6$ | Bovine | $3.00 \times 10^1$ pfu/ml (1, 1, 1) | 0 | Neg. | 16 | 8000 |

[a] Dose of challenge virus expressed as plaque forming units (PFU).
[b] Number of PFU per ml of serum. The dpc value is the day after challenge that the maximum level of viremia was detected; the onset value is the first day postchallenge that viremia was detected; and the duration value is the number of days of viremia.
[c] Porcine: number of toes with lesions plus the snout and tongue combined, if lesion present. The maximum score is 17. The day of onset is the first day after challenge that lesions were detected. Bovine: number of feet with lesions plus the tongue/nose in sites other than inoculation combined, if lesion present. The maximum score is 5
[d] Number of PFU per ml of nasal secretion. The dpc, onset and duration values are as defined in footnote b.
[e] The neutralizing antibodies is reported as the serum dilution yielding a 70% reduction in the number of plaques ($PRN_{70}$).
[f] Neg., less than 5 PFU/ml.

Example 9

Plaque Reduction Neutralization Assay

Serum samples were heated at 56° C. for 30 min, and aliquots were stored at −70° C. Sera were tested for the presence of neutralizing antibodies against FMDV in a plaque reduction neutralization assay (Mason et al., supra). Neutralizing titers were reported as the serum dilution yielding a 70% reduction in the number of plaques. Heparinized blood was collected on the day of challenge (0 dpc) and daily for the first 7 dpc, and aliquots were frozen at −70° C. Viremia was determined by a standard plaque assay of BHK-21 cells. Plasma was obtained by centrifugation of heparinized blood at 2,500 rpm for 10 min and examined for antiviral activity and for the level of pIFN-α and pIFN-γ by ELISA as described below. Nasal swab specimens were obtained on the day of challenge and daily for 7 days after challenge. Virus was isolated from the swab samples by duplicate inoculation of monolayers of IBRS-2 cells in 24-well plates. The monolayers were incubated at 37° C. with 5% $CO_2$ and examined at 24, 48, and 72 h for cytopathic effect. Negative samples were frozen and thawed, and a second passage was performed. For positive samples, titration was performed from the original samples by a standard plaque assay of BHK-21 cells.

Example 10

Protection of Swine Inoculated with FMDV A12#49

In order to determine if the immune response elicited by inoculation of swine with A12#49 was sufficient to protect against virulent FMDV infection, the inoculated animals were challenged ID with $10^5$ pfu of WT A12-IC FMDV in the right heel bulb at 21 dpi. Table 2 summarizes the results of this experiment. No clinical signs, viremia or virus shedding in nasal swabs were detected in any of the 9 animals in the 3 vaccinated groups (3 with $10^5$, 3 with $10^6$ and 3 with $10^7$ pfu of A12#49). The levels of neutralizing antibodies remained high, e.g., ~2000 $PRN_{70}$. These results indicated that inoculation of swine with the SAP double mutant conferred full protection against homologous challenge.

TABLE 2

Clinical outcome and presence of neutralizing antibodies in animals challenged with FMDV A12-IC WT 21 days after FMDV A12#49 SAP mutant inoculation.

| Group | Re-challenge virus | Dose[a] | Viremia (dpc, day of onset, duration)[b] | PFU in nasal swabs (dpc, day of onset, duration)[c] | Neutralizing antibodies $PRN_{70}$[d] 7 dpc |
|---|---|---|---|---|---|
| A12#49 SAP mutant $1 \times 10^5$ | A12-IC WT | $1 \times 10^5$ | Neg[e] | Neg. | 2000 |
| A12#49 SAP mutant $1 \times 10^6$ | A12-IC WT | $1 \times 10^5$ | Neg. | Neg. | 2000 |
| A12#49 SAP mutant $1 \times 10^7$ | A12-IC WT | $1 \times 10^5$ | Neg. | Neg. | 2000 |

[a] Dose of challenge virus expressed as number of plaque forming units (PFU).
[b] Number of PFU per ml of serum. The dpc value is the day after challenge that the maximum level of viremia was detected; the onset value is the first day postchallenge that viremia was detected; and the duration value is the number of days of viremia.
[c] Number of PFU per ml of nasal secretion. The dpc, onset and duration values are as defined in footnote b.
[d] The neutralizing antibody is reported as the serum dilution yielding a 70% reduction in the number of plaques ($PRN_{70}$).
[e] Neg., negative (less than 5 PFU/ml).

Example 11

Vaccination with FMDV SAP Mutant

Confers Early Protection Against Wild Type Virus Challenge

Eighteen 20-30 kg Yorkshire cross or Yorkshire bluepoint gilts were housed in groups of three each and were vaccinated with $1\times10^6$ pfu/ml of A12#49 (SAP mutant virus) subcutaneously (sc). At different days post-vaccination (dpv) (2, 4, 7, 14 and 21 dpv), animals were intradermally (ID) challenged with A12-FMDV wild type (WT) ($5\times10^5$ pfu/animal). Rectal temperatures and clinical signs, including lameness and vesicular lesions, were monitored daily during the first week after challenge and samples of plasma and nasal swabs were collected on a daily basis to isolate virus. Serum samples were collected at days 2, 4, 7, 14 and 21 dpv (when applicable, See Table 3) and at days 4, 7, 14 and 21 post-challenge (dpc) for the detection of neutralizing antibodies. Plasma and serum were frozen without treatment; but nasal swab specimens were collected in 2.5 ml MEM containing 2% antibiotics, 0.2% bovine serum albumin (BSA) and 20 mM Hepes buffer and clarified for 10 min at 12,600 g prior to freezing. Clinical scores were determined by the number of toes presenting typical FMD vesicular lesions plus the presence of lesions in the snout and/or mouth. The maximum score was 17, and lesions restricted to the site of challenge were not counted.

As summarized in Table 3, all but one (animal #5) swine inoculated with A12#49 (SAP mutant) were protected against wild type A12-FMDV challenge as early as 2 and for at least 21 dpv. Control animals, inoculated with PBS, developed lesions by 1-2 days post challenge reaching high scores, 13 to 17 lesions. Consistently, viremia and virus shedding in nasal swabs was detected in the same control group. Animal #5 developed FMD lesions, but relatively late as compared to the controls (5 dpc), reaching a low score (3) when no viremia was detectable. Despite the lack of viremia, significant antibody titers (0.9 to 1.5) were detected as early as 4 dpv in 9 out of 12 animals vaccinated with the SAP mutant.

These results indicate that vaccination with FMDV SAP mutant induces a strong innate and adaptive immunity. Induction of such level of innate immunity should correlate with early protection against infection by multiple FMDV serotypes.

TABLE 3

Vaccination with A12#49 SAP mutant induces early protection against challenge with wild type FMDV A12.

| Animal (Swine) | Challenge dpv[a] | Dose[b] | No. of lesions (day of onset) | Viremia (dpc, day of onset, duration)[d] | PFU in nasal swabs (dpc, day of onset, Duration)[e] | Neutralizing Antibodies $PRN_{70}$[f] | | | | |
|---|---|---|---|---|---|---|---|---|---|---|
| | | | | | | 2 dpv | 4 dpv | 7 dpv | 14 dpv | 21 dpv |
| 1 | 21 dpv | $5 \times 10^5$ | 0 | Neg.[g] | Neg. | 0 | 0.9 | 1.2 | 3.0 | 2.1 |
| 2 | | | 0 | Neg. | Neg. | 0 | 1.2 | 1.8 | 1.8 | 1.5 |
| 3 | | | 0 | Neg. | Neg. | 0 | 0.9 | 2.1 | 2.1 | 2.1 |
| 4 | 14 dpv | $5 \times 10^5$ | 0 | Neg. | Neg. | 0 | 0 | 0.9 | 1.5 | NA[h] |
| 5 | | | 3 (5) | Neg. | $4.0 \times 10^2$ pfu/ml (3, 3, 1) | 0 | 0.9 | 1.5 | 0.9 | NA |
| 6 | | | 0 | Neg. | Neg. | 0 | 0 | 1.5 | 1.8 | NA |
| 7 | 7 dpv | $5 \times 10^5$ | 0 | Neg. | Neg. | 0 | 1.5 | 1.8 | NA | NA |
| 8 | | | 0 | Neg. | Neg | 0 | 1.2 | 0.9 | NA | NA |
| 9 | | | 0 | Neg. | Neg | 0 | 0.9 | 1.2 | NA | NA |
| 10 | 4 dpv | $5 \times 10^5$ | 0 | Neg. | Neg. | 0 | 0 | NA | NA | NA |
| 11 | | | 0 | Neg. | Neg | 0 | 1.2 | NA | NA | NA |
| 12 | | | 0 | Neg. | Neg | 0 | 0.9 | NA | NA | NA |
| 13 | 2 dpv | $5 \times 10^5$ | 0 | Neg. | Neg. | 0 | NA | NA | NA | NA |
| 14 | | | 0 | Neg. | Neg | 0 | NA | NA | NA | NA |
| 15 | | | 0 | Neg. | Neg | 0 | NA | NA | NA | NA |
| 16 | Control | $5 \times 10^5$ | 17 (2) | $1.8 \times 10^4$ pfu/ml (3, 2, 3) | $7.0 \times 10^2$ pfu/ml (3, 3, 2) | NA | NA | NA | NA | NA |
| 17 | | | 13 (1) | $2.2 \times 10^3$ pfu/ml (3, 2, 3) | $1.4 \times 10^3$ pfu/ml (4, 3, 3) | NA | NA | NA | NA | NA |
| 18 | | | 17 (2) | $1.8 \times 10^5$ pfu/ml (3, 2, 3) | $1.9 \times 10^3$ pfu/ml (3, 3, 2) | NA | NA | NA | NA | NA |

[a]DPV: days post-vaccination when the challenge was performed.
[b]Dose of challenge virus expressed as plaque forming units (PFU).
[c]Number of toes with lesions plus the snout and tongue combined, if lesion present; maximum score = 17. Onset = first day after challenge that lesions were detected.
[d]Number of PFU per ml of serum. DPC value = day after challenge when maximum level of viremia was detected. Onset = first day post-challenge when viremia was detected. Duration = number of days of viremia.
[e]Number of PFU per ml of nasal secretion. The dpc, onset and duration values are as defined in footnote d.
[f]Neutralizing antibody titer is reported as the logarithm of the serum dilution yielding a 70% reduction in the number of plaques ($PRN_{70}$).
[g]Neg. = less than 5 PFU/ml.
[h]Data not available.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An effective live-attenuated foot-and-mouth disease (FMD) vaccine composition comprising a recombinant foot-and-mouth disease virus (FMDV) mutant comprising two single point mutations in amino acid positions 55 and 58 of the coding region of the SAF-A/B, Acinus and PIAS (SAP) domain of the leader proteinase) ($L^{pro}$) of FMDV in an effective amount to protect swine and cattle from clinical FMD when challenged with virulent FMDV.

2. The effective live-attenuated FMD vaccine composition of claim 1 wherein the recombinant FMDV mutant comprises a FMDV $L^{pro}$ having two single point mutations in amino acid positions 55 and 58 of the coding region of the SAF-A/B, Acinus and PIAS (SAP) domain of the leader proteinase ($L^{pro}$) of FMDV and additional mutation/s which results in more attenuation and a decreased probability of reversion.

3. The effective live-attenuated FMD vaccine composition of claim 1 wherein the recombinant FMDV mutant comprises a FMDV $L^{pro}$ having two single point mutations in amino acid positions 55 and 58 of the coding region of the SAP domain of the FMDV $L^{pro}$ and additional mutation/s which provides a serological distinction between vaccinated animals and animals infected with FMDV.

4. An isolated cell infected with the FMDV mutant of any one of claims 1, 2 and 3.

5. A method of immunizing swine and cattle against FMD, comprising administering to swine and cattle an effective amount of an effective live attenuated FMD vaccine composition comprising a recombinant mutant FMDV according to any one of claims 1, 2 and 3.

6. A method for the protection of swine and cattle against FMD, comprising administering to swine and cattle an effective live attenuated FMD vaccine composition comprising a recombinant mutant FMDV according to any one of claims 1, 2 and 3 in an amount effective to protect said swine and cattle from clinical FMD.

7. A method of distinguishing animals infected with FMD from animals vaccinated with an effective live attenuated FMD vaccine composition comprising a recombinant mutant FMDV according to claim 3 comprising: analyzing serum from an animal under evaluation to determine if said serum binds specifically to the mutant SAP epitope.

* * * * *

SEQUENCE LISTING

<160> NUMBER OF SEQ ID NOS: 51

<210> SEQ ID NO 1
<211> LENGTH: 37
<212> TYPE: PRT
<213> ORGANISM: Foot-and-mouth disease virus

<400> SEQUENCE: 1

Pro Glu Asn Leu Thr Leu Ala Ala Ile Lys Gln Leu Glu Glu Leu Thr
1               5                   10                  15

Gly Leu Glu Leu His Glu Gly Gly Pro Pro Ala Leu Val Ile Trp Asn
            20                  25                  30

Ile Lys His Leu Leu
        35

<210> SEQ ID NO 2
<211> LENGTH: 35
<212> TYPE: PRT
<213> ORGANISM: Foot-and-mouth disease virus

<400> SEQUENCE: 2

Ile Asp Lys Trp Lys Val Thr Glu Leu Lys Glu Glu Leu Lys Arg Arg
1               5                   10                  15

Arg Leu Thr Thr Arg Gly Leu Lys Glu Glu Leu Val Arg Arg Leu Asp
            20                  25                  30

Glu Ala Leu
        35

<210> SEQ ID NO 3
<211> LENGTH: 35
<212> TYPE: PRT
<213> ORGANISM: Foot-and-mouth disease virus

<400> SEQUENCE: 3

Leu Asn Asp Phe Ser Leu Thr Thr Leu Lys Asp Trp Leu Arg Ile Leu
1               5                   10                  15

Gly Gln Asn Thr Glu Gly Thr Lys Thr Glu Leu Ile Ala Arg Leu Gln
            20                  25                  30

Asp Ile Pro
        35

<210> SEQ ID NO 4
<211> LENGTH: 35
<212> TYPE: PRT
<213> ORGANISM: Foot-and-mouth disease virus

<400> SEQUENCE: 4

Leu Lys Lys Phe Arg Asn Ala Met Leu Lys Ser Ile Cys Glu Val Leu
1               5                   10                  15

Asp Leu Glu Arg Ser Gly Val Asn Ser Glu Leu Val Lys Arg Ile Leu
            20                  25                  30

Asn Phe Leu
        35

<210> SEQ ID NO 5
<211> LENGTH: 35
<212> TYPE: PRT
<213> ORGANISM: Foot-and-mouth disease virus

<400> SEQUENCE: 5

Glu Thr Gly Leu Ile Ile Pro Gln Leu Lys Asp Ile Leu Arg Val Phe

```
                1               5                  10                  15
Gly Leu Arg Leu Ser Gly Thr Lys Ala Glu Leu Ile Thr Arg Ile Lys
                20                  25                  30
Gln Leu Ile
        35

<210> SEQ ID NO 6
<211> LENGTH: 35
<212> TYPE: PRT
<213> ORGANISM: Foot-and-mouth disease virus

<400> SEQUENCE: 6

Leu Gln Ala Leu Arg Val Thr Asp Leu Lys Ala Ala Leu Glu Gln Arg
1               5                   10                  15
Gly Leu Ala Lys Ser Gly Gln Lys Ser Ala Leu Val Lys Arg Leu Lys
                20                  25                  30
Gly Ala Leu
        35

<210> SEQ ID NO 7
<211> LENGTH: 35
<212> TYPE: PRT
<213> ORGANISM: Foot-and-mouth disease virus

<400> SEQUENCE: 7

Leu Ser Ser Leu Lys Val Thr Glu Leu Lys Glu Leu Glu Asn Arg
1               5                   10                  15
Gln Leu Ser Thr Lys Gly Val Lys Ala Val Leu Gln Glu Arg Leu Arg
                20                  25                  30
Glu Ala Leu
        35

<210> SEQ ID NO 8
<211> LENGTH: 35
<212> TYPE: PRT
<213> ORGANISM: Foot-and-mouth disease virus

<400> SEQUENCE: 8

Val Met Ser Phe Arg Val Ser Asp Leu Gln Met Leu Leu Gly Phe Val
1               5                   10                  15
Gly Arg Ser Lys Ser Gly Leu Lys His Glu Leu Val Thr Arg Ala Leu
                20                  25                  30
Gln Leu Val
        35

<210> SEQ ID NO 9
<211> LENGTH: 35
<212> TYPE: PRT
<213> ORGANISM: Foot-and-mouth disease virus

<400> SEQUENCE: 9

Leu Ser Glu Leu Arg Val Ile Asp Leu Arg Ala Glu Leu Lys Lys Arg
1               5                   10                  15
Asn Leu Asp Thr Gly Gly Asn Lys Ser Val Leu Met Glu Arg Leu Lys
                20                  25                  30
Lys Ala Val
        35

<210> SEQ ID NO 10
<211> LENGTH: 35
```

```
<212> TYPE: PRT
<213> ORGANISM: Foot-and-mouth disease virus

<400> SEQUENCE: 10

Val Met Ser Leu Arg Val Ser Glu Leu Gln Val Leu Gly Tyr Ala
1               5                   10                  15

Gly Arg Asn Lys His Gly Arg Lys His Glu Leu Leu Thr Lys Ala Leu
            20                  25                  30

His Leu Leu
        35

<210> SEQ ID NO 11
<211> LENGTH: 35
<212> TYPE: PRT
<213> ORGANISM: Foot-and-mouth disease virus

<400> SEQUENCE: 11

Tyr Ala Leu Leu Ser Glu Ser Lys Ile Arg Ser Lys Leu Ser Glu Met
1               5                   10                  15

Gly Leu Pro Thr Asp Gly His Lys Gln Leu Leu Gln Arg Arg His Ala
            20                  25                  30

Lys Trp Val
        35

<210> SEQ ID NO 12
<211> LENGTH: 35
<212> TYPE: PRT
<213> ORGANISM: Foot-and-mouth disease virus

<400> SEQUENCE: 12

Tyr Ser Leu Leu Lys Asp Thr Val Leu Arg Lys Lys Leu Lys Asp Leu
1               5                   10                  15

Gly Ile Pro Asn Trp Gly Pro Arg Ala Leu Leu Gln Arg Arg His Thr
            20                  25                  30

Glu Trp Leu
        35

<210> SEQ ID NO 13
<211> LENGTH: 35
<212> TYPE: PRT
<213> ORGANISM: Foot-and-mouth disease virus

<400> SEQUENCE: 13

Leu Gly Lys Leu Thr Val Pro Thr Leu Lys Asp Ile Cys Lys Ala His
1               5                   10                  15

Gly Leu Lys Ser Gly Pro Lys Lys Gln Glu Leu Leu Asp Ala Leu Ile
            20                  25                  30

Arg His Leu
        35

<210> SEQ ID NO 14
<211> LENGTH: 35
<212> TYPE: PRT
<213> ORGANISM: Foot-and-mouth disease virus

<400> SEQUENCE: 14

Val Leu Asn Met Thr Cys Asp Lys Leu Arg Lys Glu Leu Lys Lys Lys
1               5                   10                  15

Arg Ala Ser Thr Ala Gly Lys Lys Ser Glu Leu Gln Ser Arg Leu Leu
            20                  25                  30
```

```
Glu Phe Leu
        35

<210> SEQ ID NO 15
<211> LENGTH: 35
<212> TYPE: PRT
<213> ORGANISM: Foot-and-mouth disease virus

<400> SEQUENCE: 15

Tyr Ser Ile Val Arg Asp Thr Ala Leu Arg Lys Lys Leu Ser Glu Leu
1               5                   10                  15

Gly Leu Ser Thr His Gly Ser Arg Gln Leu Leu Glu Lys Arg His Lys
            20                  25                  30

Glu Trp Ile
        35

<210> SEQ ID NO 16
<211> LENGTH: 35
<212> TYPE: PRT
<213> ORGANISM: Foot-and-mouth disease virus

<400> SEQUENCE: 16

Ala Ser Lys Met Val Val Ser Glu Leu Lys Glu Glu Leu Glu Ala Gln
1               5                   10                  15

Gly Leu Pro Ile Asp Gly Thr Arg Asn Val Leu Tyr Gln Arg Val Gln
            20                  25                  30

Lys Ala Arg
        35

<210> SEQ ID NO 17
<211> LENGTH: 35
<212> TYPE: PRT
<213> ORGANISM: Foot-and-mouth disease virus

<400> SEQUENCE: 17

Val Lys Lys Leu Lys Val Ser Glu Leu Lys Glu Glu Leu Lys Lys Arg
1               5                   10                  15

Arg Leu Ser Asp Lys Gly Leu Lys Ala Asp Leu Met Glu Arg Leu Gln
            20                  25                  30

Ala Ala Leu
        35

<210> SEQ ID NO 18
<211> LENGTH: 35
<212> TYPE: PRT
<213> ORGANISM: Foot-and-mouth disease virus

<400> SEQUENCE: 18

Ile Lys Ala Leu Lys Val Ser Gln Leu Lys Asp Ile Leu Arg Asp Arg
1               5                   10                  15

Gly Leu Arg Val Ser Gly Lys Lys Ala Asp Leu Leu Asp Asn Leu Thr
            20                  25                  30

Asn Tyr Val
        35

<210> SEQ ID NO 19
<211> LENGTH: 35
<212> TYPE: PRT
<213> ORGANISM: Foot-and-mouth disease virus

<400> SEQUENCE: 19
```

-continued

```
Val Arg Arg Leu Lys Val Asn Glu Leu Arg Glu Leu Gln Arg Arg
1               5                  10                  15

Gly Leu Asp Thr Arg Gly Leu Lys Thr Glu Leu Ala Glu Arg Leu Gln
                20                  25                  30

Ala Ala Leu
        35

<210> SEQ ID NO 20
<211> LENGTH: 35
<212> TYPE: PRT
<213> ORGANISM: Foot-and-mouth disease virus

<400> SEQUENCE: 20

Met Asp Thr Met Thr Ala Glu Gln Leu Lys Gln Ala Leu Met Lys Ile
1               5                  10                  15

Lys Val Ser Thr Gly Gly Asn Lys Lys Thr Leu Arg Lys Arg Val Ala
                20                  25                  30

Gln Tyr Tyr
        35

<210> SEQ ID NO 21
<211> LENGTH: 35
<212> TYPE: PRT
<213> ORGANISM: Foot-and-mouth disease virus

<400> SEQUENCE: 21

Met Ala Pro Gly Ala Ala Gln Glu Leu Gln Ala Lys Leu Ala Glu Ile
1               5                  10                  15

Gly Ala Pro Ile Gln Gly Asn Arg Glu Glu Leu Val Glu Arg Leu Gln
                20                  25                  30

Ser Tyr Thr
        35

<210> SEQ ID NO 22
<211> LENGTH: 35
<212> TYPE: PRT
<213> ORGANISM: Foot-and-mouth disease virus

<400> SEQUENCE: 22

Ile Thr Asp Leu Arg Val Ile Asp Leu Lys Ser Glu Leu Lys Arg Arg
1               5                  10                  15

Asn Leu Asp Ile Thr Gly Val Lys Thr Val Leu Ile Ser Arg Leu Lys
                20                  25                  30

Gln Ala Ile
        35

<210> SEQ ID NO 23
<211> LENGTH: 35
<212> TYPE: PRT
<213> ORGANISM: Foot-and-mouth disease virus

<400> SEQUENCE: 23

Phe Ser Ser Leu Ser Thr Gln Lys Ile Lys Ala Lys Leu Ser Asp Leu
1               5                  10                  15

Lys Leu Pro Thr Thr Gly Ser Arg Asn Glu Met Glu Ala Arg Tyr Leu
                20                  25                  30

His Tyr Tyr
        35

<210> SEQ ID NO 24
```

<211> LENGTH: 35
<212> TYPE: PRT
<213> ORGANISM: Foot-and-mouth disease virus

<400> SEQUENCE: 24

Leu Gly Lys Leu Thr Val Ser Ala Leu Lys Asp Thr Cys Arg His Tyr
1               5                   10                  15
Gly Leu Arg Ser Gly Gly Lys Lys Gln Glu Leu Ile Asp Ala Leu Thr
                20                  25                  30
Glu Tyr Phe
        35

<210> SEQ ID NO 25
<211> LENGTH: 35
<212> TYPE: PRT
<213> ORGANISM: Foot-and-mouth disease virus

<400> SEQUENCE: 25

Phe Thr Ser Met Thr Gln Ser Gln Ile Lys Gln Lys Leu Ser Ser Leu
1               5                   10                  15
Gly Leu Ser Thr Asn Gly Thr Arg Gln Asn Met Ile Lys Arg Tyr Asn
                20                  25                  30
His Tyr Glu
        35

<210> SEQ ID NO 26
<211> LENGTH: 35
<212> TYPE: PRT
<213> ORGANISM: Foot-and-mouth disease virus

<400> SEQUENCE: 26

Val Gln Met Leu Arg Val Val Glu Leu Gln Lys Ile Leu Ser Phe Leu
1               5                   10                  15
Asn Ile Ser Phe Ala Gly Arg Lys Thr Asp Leu Gln Ser Arg Ile Leu
                20                  25                  30
Ser Phe Leu
        35

<210> SEQ ID NO 27
<211> LENGTH: 35
<212> TYPE: PRT
<213> ORGANISM: Foot-and-mouth disease virus

<400> SEQUENCE: 27

Leu Ala Ser Leu Thr Val Ser Val Leu Arg Asp Phe Cys Lys Gln Glu
1               5                   10                  15
Gly Leu Arg Cys Pro Ser Lys Lys Ala Glu Ile Val Asp Cys Ile Lys
                20                  25                  30
Lys His Leu
        35

<210> SEQ ID NO 28
<211> LENGTH: 35
<212> TYPE: PRT
<213> ORGANISM: Foot-and-mouth disease virus

<400> SEQUENCE: 28

Tyr Asn Leu Leu Ser Asp Arg Asp Leu Lys Lys Leu Lys Gln Tyr
1               5                   10                  15
Gly Leu Ser Val Pro Gly Asn Lys Gln Gln Leu Ile Lys Arg His Gln
                20                  25                  30

-continued

```
Glu Phe Val
        35

<210> SEQ ID NO 29
<211> LENGTH: 35
<212> TYPE: PRT
<213> ORGANISM: Foot-and-mouth disease virus

<400> SEQUENCE: 29

Tyr Ser Ser Leu Thr Val Val Gln Leu Lys Asp Leu Leu Thr Lys Arg
1               5                   10                  15

Asn Leu Ser Val Gly Gly Leu Lys Asn Glu Leu Val Gln Arg Leu Ile
            20                  25                  30

Lys Asp Asp
        35

<210> SEQ ID NO 30
<211> LENGTH: 35
<212> TYPE: PRT
<213> ORGANISM: Foot-and-mouth disease virus

<400> SEQUENCE: 30

Tyr Lys Ser Leu Lys Val Ala Glu Leu Arg Glu Lys Leu Ala Glu Lys
1               5                   10                  15

Gly Leu Ser Thr Ala Gly Asn Lys Ala Glu Leu Val Ser Arg Leu Thr
            20                  25                  30

Ala Ala Thr
        35

<210> SEQ ID NO 31
<211> LENGTH: 35
<212> TYPE: PRT
<213> ORGANISM: Foot-and-mouth disease virus

<400> SEQUENCE: 31

Phe Gln Lys Phe Thr Val Lys Val Leu Lys Glu Gln Cys Lys Ser Arg
1               5                   10                  15

Gly Leu Lys Leu Ser Gly Arg Lys Ser Asp Leu Leu Gln Arg Leu Ile
            20                  25                  30

Thr His Asp
        35

<210> SEQ ID NO 32
<211> LENGTH: 35
<212> TYPE: PRT
<213> ORGANISM: Foot-and-mouth disease virus

<400> SEQUENCE: 32

Ser Ala Arg Leu Arg Val Ala Asp Val Arg Ala Glu Leu Gln Arg Arg
1               5                   10                  15

Gly Leu Asp Val Ser Gly Thr Lys Pro Ala Leu Val Arg Arg Leu Asp
            20                  25                  30

Ala Ala Ile
        35

<210> SEQ ID NO 33
<211> LENGTH: 35
<212> TYPE: PRT
<213> ORGANISM: Foot-and-mouth disease virus

<400> SEQUENCE: 33
```

-continued

Ile Glu Ala Met Thr Val Gln Glu Leu Arg Ser Thr Leu Arg Lys Leu
1               5                   10                  15

Gly Val Pro Val Lys Gly Arg Lys Gln Glu Leu Ile Ser Thr Leu Arg
            20                  25                  30

Leu His Met
        35

<210> SEQ ID NO 34
<211> LENGTH: 35
<212> TYPE: PRT
<213> ORGANISM: Foot-and-mouth disease virus

<400> SEQUENCE: 34

Pro Lys Thr Met Lys Val Asn Asp Leu Arg Lys Glu Leu Glu Ser Arg
1               5                   10                  15

Ala Leu Ser Ser Lys Gly Leu Lys Ser Gln Leu Ile Ala Arg Leu Thr
            20                  25                  30

Lys Gln Leu
        35

<210> SEQ ID NO 35
<211> LENGTH: 35
<212> TYPE: PRT
<213> ORGANISM: Foot-and-mouth disease virus

<400> SEQUENCE: 35

Met Ala Thr Val Lys Leu Ser Phe Leu Gln His Ile Cys Lys Leu Thr
1               5                   10                  15

Gly Leu Ser Arg Ser Gly Arg Lys Asp Glu Leu Leu Arg Arg Ile Val
            20                  25                  30

Asp Ser Pro
        35

<210> SEQ ID NO 36
<211> LENGTH: 35
<212> TYPE: PRT
<213> ORGANISM: Foot-and-mouth disease virus

<400> SEQUENCE: 36

Met Glu Gln Leu Lys Val Leu Glu Leu Lys Gln Ile Cys Lys Ser Leu
1               5                   10                  15

Asp Leu Ser Ile Thr Gly Lys Lys Ala Val Leu Gln Asp Arg Ile Lys
            20                  25                  30

Gln Phe Leu
        35

<210> SEQ ID NO 37
<211> LENGTH: 35
<212> TYPE: PRT
<213> ORGANISM: Foot-and-mouth disease virus

<400> SEQUENCE: 37

Val Pro Leu Leu Pro Lys Asn Arg Leu Val Lys Glu Leu Gln Asp Arg
1               5                   10                  15

Gly Leu Asp Thr Ser Gly Val Gln Thr Val Leu Ala Asp Arg Leu Val
            20                  25                  30

Glu Phe Leu
        35

```
<210> SEQ ID NO 38
<211> LENGTH: 35
<212> TYPE: PRT
<213> ORGANISM: Foot-and-mouth disease virus

<400> SEQUENCE: 38

Leu Glu Gly Met Ser Tyr Arg Glu Leu Gln Gly Leu Ala Lys Ala Arg
1               5                   10                  15

Gly Val Ala Ala Asn Gly Gly Lys Lys Asp Val Ile Gln Arg Leu Leu
            20                  25                  30

Ser Ala Thr
        35

<210> SEQ ID NO 39
<211> LENGTH: 35
<212> TYPE: PRT
<213> ORGANISM: Foot-and-mouth disease virus

<400> SEQUENCE: 39

Ile Lys Lys Val Asp Asn Lys Gly Leu Arg Ser Ile Cys Glu Ile Leu
1               5                   10                  15

Thr Leu Asp Arg Lys Gly Ser Lys Asn Glu Thr Val Leu Arg Val Leu
            20                  25                  30

Lys Phe Leu
        35

<210> SEQ ID NO 40
<211> LENGTH: 35
<212> TYPE: PRT
<213> ORGANISM: Foot-and-mouth disease virus

<400> SEQUENCE: 40

Leu His Lys Leu Lys Leu Ala Glu Leu Lys Gln Glu Cys Leu Ala Arg
1               5                   10                  15

Gly Leu Glu Thr Lys Gly Ile Lys Gln Asp Leu Ile His Arg Leu Gln
            20                  25                  30

Ala Tyr Leu
        35

<210> SEQ ID NO 41
<211> LENGTH: 35
<212> TYPE: PRT
<213> ORGANISM: Foot-and-mouth disease virus

<400> SEQUENCE: 41

Phe Arg Gly Met Ile Val Lys Glu Leu Arg Glu Glu Ala Ile Lys Arg
1               5                   10                  15

Gly Leu Asp Thr Thr Gly Thr Lys Lys Asp Leu Leu Glu Arg Leu Cys
            20                  25                  30

Asn Asp Ala
        35

<210> SEQ ID NO 42
<211> LENGTH: 35
<212> TYPE: PRT
<213> ORGANISM: Foot-and-mouth disease virus

<400> SEQUENCE: 42

Met Glu Leu Leu Lys Val Ser Glu Leu Lys Asp Ile Cys Arg Ser Val
1               5                   10                  15

Ser Phe Pro Val Ser Gly Arg Lys Ala Val Leu Gln Asp Leu Ile Arg
```

Asn Phe Leu
        35

<210> SEQ ID NO 43
<211> LENGTH: 35
<212> TYPE: PRT
<213> ORGANISM: Foot-and-mouth disease virus

<400> SEQUENCE: 43

Ala Asn Lys Leu Lys Val Asp Glu Leu Arg Leu Lys Leu Ala Glu Arg
1               5                   10                  15

Gly Leu Ser Thr Thr Gly Val Lys Ala Val Leu Val Glu Arg Leu Glu
            20                  25                  30

Glu Ala Ile
        35

<210> SEQ ID NO 44
<211> LENGTH: 35
<212> TYPE: PRT
<213> ORGANISM: Foot-and-mouth disease virus

<400> SEQUENCE: 44

Pro Lys Ser Met Lys Val Ala Glu Leu Arg Val Glu Leu Glu Leu Arg
1               5                   10                  15

Gly Leu Glu Thr Lys Gly Ile Lys Thr Leu Leu Val Gln Arg Leu Gln
            20                  25                  30

Thr Ala Leu
        35

<210> SEQ ID NO 45
<211> LENGTH: 34
<212> TYPE: PRT
<213> ORGANISM: Foot-and-mouth disease virus

<400> SEQUENCE: 45

Asx Pro Pro Leu Pro Leu Ser Cys Leu Pro Asx Leu Cys Pro Asx Gly
1               5                   10                  15

Leu Ser Ser Ser Gly Pro Lys Ser Pro Leu Leu Pro Arg Leu Pro Pro
            20                  25                  30

Asx Leu

<210> SEQ ID NO 46
<211> LENGTH: 42
<212> TYPE: DNA
<213> ORGANISM: Artificial Sequence
<220> FEATURE:
<223> OTHER INFORMATION: Chemically Synthesized

<400> SEQUENCE: 46
ctcacactag cagccgccaa acagctggag gaactcacag gg                          42

<210> SEQ ID NO 47
<211> LENGTH: 42
<212> TYPE: DNA
<213> ORGANISM: Artificial Sequence
<220> FEATURE:
<223> OTHER INFORMATION: Chemically Synthesized

<400> SEQUENCE: 47
ccctgtgagt tcctccagct gtttggcggc tgctagtgtg ag                          42

```
<210> SEQ ID NO 48
<211> LENGTH: 42
<212> TYPE: DNA
<213> ORGANISM: Artificial Sequence
<220> FEATURE:
<223> OTHER INFORMATION: Chemically Synthesized

<400> SEQUENCE: 48
ctcacactag cagccatcaa acaggcggag gaactcacag gg                          42

<210> SEQ ID NO 49
<211> LENGTH: 42
<212> TYPE: DNA
<213> ORGANISM: Artificial Sequence
<220> FEATURE:
<223> OTHER INFORMATION: Chemically Synthesized

<400> SEQUENCE: 49
ccctgtgagt tcctccgcct gtttgatggc tgctagtgtg ag                          42

<210> SEQ ID NO 50
<211> LENGTH: 42
<212> TYPE: DNA
<213> ORGANISM: Artificial Sequence
<220> FEATURE:
<223> OTHER INFORMATION: Chemically Synthesized

<400> SEQUENCE: 50
ctcacactag cagccgccaa acaggcggag gaactcacag gg                          42

<210> SEQ ID NO 51
<211> LENGTH: 42
<212> TYPE: DNA
<213> ORGANISM: Artificial Sequence
<220> FEATURE:
<223> OTHER INFORMATION: Chemically Synthesized

<400> SEQUENCE: 51
ccctgtgagt tcctccgcct gtttggcggc tgctagtgtg ag                          42
```